United States Patent
Hudson

(10) Patent No.: US 8,486,435 B2
(45) Date of Patent: Jul. 16, 2013

(54) CORE-SHEATH IMPLANT DEVICE HAVING AN INNER CORE LOBE

(75) Inventor: Michael E. Hudson, Hayden, AL (US)

(73) Assignee: Evonik Corporation, Parsippany, NJ (US)

( * ) Notice: Subject to any disclaimer, the term of this patent is extended or adjusted under 35 U.S.C. 154(b) by 9 days.

(21) Appl. No.: 13/171,927

(22) Filed: Jun. 29, 2011

(65) Prior Publication Data

US 2012/0004724 A1    Jan. 5, 2012

Related U.S. Application Data

(60) Provisional application No. 61/360,140, filed on Jun. 30, 2010.

(51) Int. Cl.
*A61F 2/02* (2006.01)

(52) U.S. Cl.
USPC .................................................. 424/423

(58) Field of Classification Search
None
See application file for complete search history.

(56) References Cited

U.S. PATENT DOCUMENTS

| | | | |
|---|---|---|---|
| 4,180,560 A | 12/1979 | Katz et al. | |
| 5,891,456 A | 4/1999 | Shah et al. | |
| 7,052,710 B2 | 5/2006 | Giordano et al. | |
| 2006/0003006 A1 | 1/2006 | Remon et al. | |

FOREIGN PATENT DOCUMENTS

| | | |
|---|---|---|
| WO | WO-03/000156 A1 | 1/2003 |
| WO | WO-2010/111627 A1 | 9/2010 |

OTHER PUBLICATIONS

International Search Report and Written Opinion issued on Apr. 23, 2012 for Intl. App. No. PCT/US2011/042314, filed on Jun. 29, 2011 (Inventor—M. Hudson; Applicant—Surmodics Pharmaceuticals, Inc.; pp. 1-9).

*Primary Examiner* — Carlos Azpuru
(74) *Attorney, Agent, or Firm* — Linda S. Li; Jason S. Ngui

(57) ABSTRACT

The core-sheath implant device allows for a bioactive agent release profile that can be tailored to a particular therapy. The device features one or more lobes extending from an inner core at least partially through the outer sheath. Depending on the particular design of such an implant device, a variety of release profiles can be achieved.

10 Claims, 5 Drawing Sheets

CORE-SHEATH IMPLANT DEVICE HAVING AN INNER CORE LOBE

CROSS-REFERENCE TO RELATED APPLICATIONS

This Application claims the benefit of priority from prior U.S. Provisional Application No. 61/360,140, filed Jun. 30, 2010, the entire contents of which are incorporated into this Application by reference.

BACKGROUND

Biodegradable implant devices often include a biocompatible polymeric matrix or biodegradable polymeric matrix that includes a bioactive agent dispersed or localized in the matrix. The bioactive agent can be released from the matrix through a number of different mechanisms and release profiles. These implant devices are very useful in providing a release profile tailored to a particular therapy. For example, implant devices can provide a prolonged release profile to release a bioactive agent over a period of time, such as days or even months.

Implant devices are compatible with most classes of bioactive agents. However, the current design of many implant devices limits the number of different release profiles that can be achieved for a particular bioactive agent. Accordingly, a need exists for improved implant devices featuring new designs that allow for flexibility in tailoring a release profile to a particular therapy. These needs and other needs are satisfied by the present invention.

SUMMARY

The implant devices comprises an outer sheath comprising a biocompatible polymer and having an exposed longitudinal sheath surface and exposed proximal and distal end surfaces; and an inner core comprising a bioactive agent and having: i. a longitudinal core surface that is completely surrounded by the sheath; and ii. a longitudinal lobe extending outwardly from the longitudinal core surface at least partially through the outer sheath and having a longitudinal lobe surface; wherein at least a portion of the longitudinal lobe surface is closer to the exposed longitudinal sheath surface than any portion of the longitudinal core surface.

DETAILED DESCRIPTION

Figure 1A:
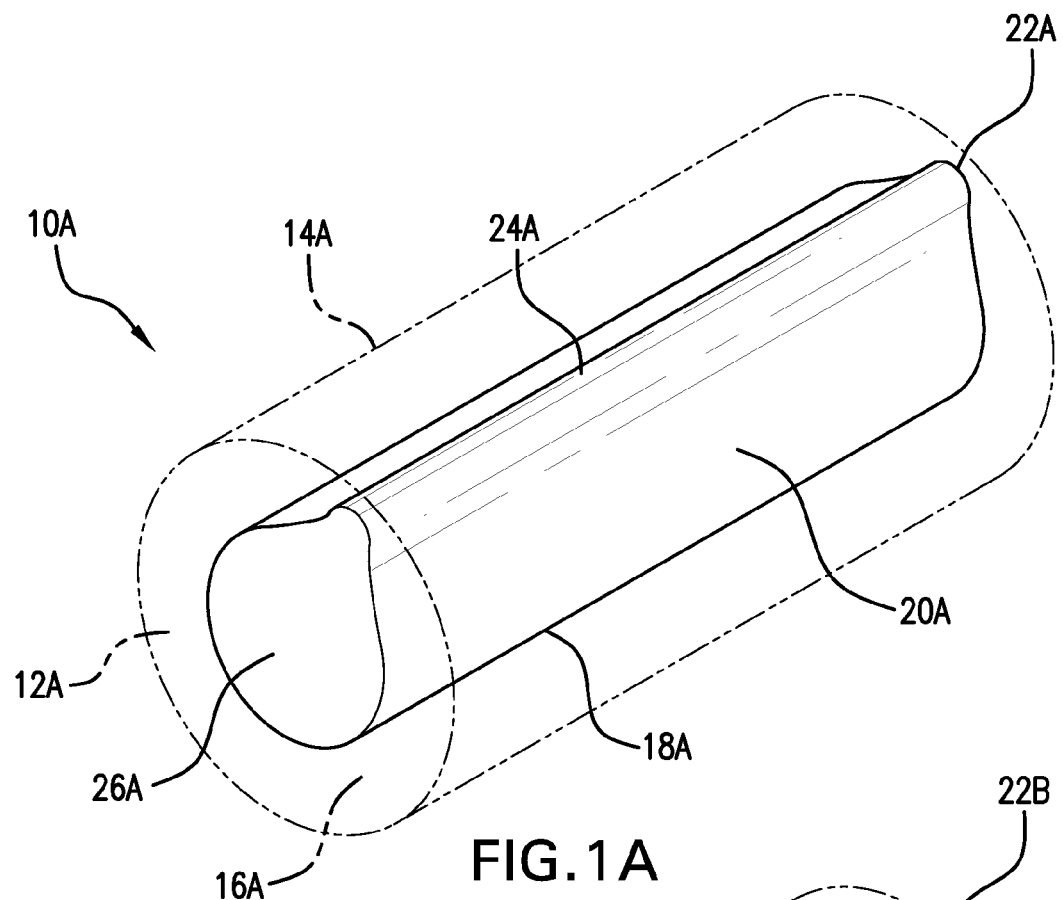
FIG. 1A is an isometric view of an implant device having a core lobe that extends partially through the outer sheath. The outer sheath is shown in phantom line to indicate that the outer sheath can have any geometry.

The following terms are used in this application and have the following meanings:

The word "comprise," or variations such as "comprises" or "comprising," implies the inclusion of the stated component or step but not the exclusion of any other component or step.

The singular forms "a," "an" and "the" include plural references unless the context clearly dictates otherwise.

A "weight percent" of a component, unless specifically stated to the contrary, is based on the total weight of the formulation or composition in which the component is included.

"Optional" or "optionally" means that the subsequently described event or circumstance can or cannot occur.

Ranges can be expressed as from or to "about" a particular value. Such a range includes a range that is from or to the specific particular value and ranges that are from or to "about" the particular value. For example, a range that is from "about" 1 to "about" 2 includes the range that is from 1 to 2, as well as ranges that are from about 1 to about 2. Ranges, in general, are intended to include all of the integers within the range, including the endpoints.

The term "implant device," refers to any article that is at least 1 mm in length in at least one dimension of the device. For example, the device can have one dimension that is from 1 mm to 50 mm, 1.2 mm to 45 mm, 1.4 mm to 42 mm, 1.6 mm to 40 mm, 1.8 mm to 38 mm, or 2.0 mm to 36 mm, 5.0 mm to 33 mm, or 10 mm to 30 mm. Other examples include implant devices having one dimension that is at least 3 cm, or up to or greater than 10 cm, 20 cm, or even 30 cm. The diameter of the implant device can be any dimension, for example, from 1 mm to 50 mm.

The term "biocompatible" refers to a substance and its degradation products that are substantially non-toxic to a subject.

"Biodegradable" refers a material that will erode to soluble species or that will degrade under physiologic conditions to smaller units or chemical species that are themselves non-toxic (biocompatible) to a subject and capable of being metabolized, eliminated, or excreted by the subject.

A "bioactive agent" refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. Bioactive agents also include agents that affect the structure or function of a subject (including pro-drugs) which become bioactive or more bioactive after being placed in a predetermined physiological environment.

An "exposed" surface refers to an outer surface that is exposed to the atmosphere or another surrounding medium when the implant device is in use, such as a bodily fluid or tissue.

A "sheath" refers to a covering of the inner core that surrounds at least a portion of the inner core along the longitudinal axis of the device. The "sheath" can have a single or multiple layers.

The implant devices of the invention allow for a bioactive agent release profile that can be tailored to a particular therapy. Unlike typical core-sheath implants, the implant devices of the invention feature one or more lobes extending from the core at least partially through the outer sheath. Depending on the particular design of such an implant device, a variety of release profiles can be achieved. Since the core extends at least partially through the outer sheath, the bioactive agent in the core may diffuse outwardly toward the exposed surface. Such a diffusion pathway may increase the release rate of the bioactive agent from certain locations of the implant device. The diffusion pathway from the inner core to the exposed surface can be altered by changing the design of the inner core and outer sheath.

Referring now to FIG. 1A, implant device 10A comprises outer sheath 12A having exposed longitudinal sheath surface 14A, exposed proximal end surface 16A, and an exposed distal end surface (not shown). Outer sheath 12A partially or fully surrounds inner core 18A. Inner core 18A defines longitudinal core surface 20A that is completely surrounded by outer sheath 12A. Longitudinal lobe 22A extends outwardly from longitudinal core surface 20A partially through outer sheath 12A. Longitudinal lobe 22A defines longitudinal lobe surface 24A.

Inner core 18A also defines proximal end surface 26A and a distal end surface (not shown). Proximal end surface 26A or the distal end surface can be surrounded by outer sheath 12A. Or either of these surfaces can be exposed surfaces. When both proximal end surface 26A and the distal end surface (not shown) is exposed and substantially flush with exposed core proximal sheath end surface 16A and the exposed distal sheath end surface (not shown), inner core 18A is substantially coextensive with outer sheath 12A.

At least a portion of longitudinal lobe surface 24A is closer to exposed longitudinal sheath surface 14A than any portion of longitudinal core surface 20A. Longitudinal lobe 22A can extend any distance through outer sheath 12A. In FIG. 1A, longitudinal lobe 22A extends away from inner core surface 20A toward exposed longitudinal sheath surface 14A but does not extend completely through outer sheath 12A, i.e., outer sheath 12A surrounds not only longitudinal core surface 20A but also lobe surface 24A. But lobe surface 24A is closer to longitudinal sheath surface 14A than any portion of longitudinal core surface 20A.

Figure 1B:
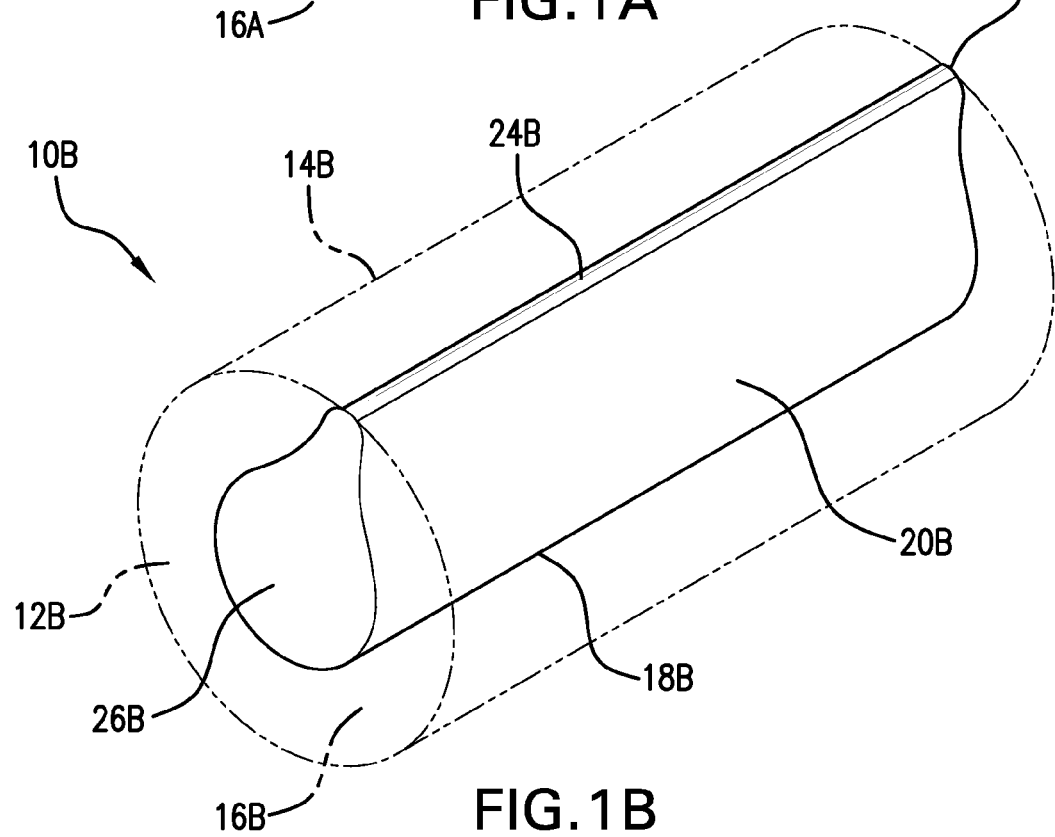
FIG. 1B is an isometric view of an implant device having a core lobe that extends completely through the outer sheath and defines an exposed longitudinal core surface. Again, the outer sheath is shown in phantom line.

In contrast, longitudinal lobe 22A can extend completely through outer sheath 12A. With reference to FIG. 1B, for example, implant device 10B includes all the elements shown in FIG. 1A (outer sheath 12B, sheath surface 14B, end surface 16B, inner core 18B, core surface 20B, end surface 26B), with longitudinal lobe 22B extending completely through outer sheath 12B and defining longitudinal lobe surface 24B that in this instance is an exposed surface that is not surrounded by outer sheath 12B.

Figure 1C:
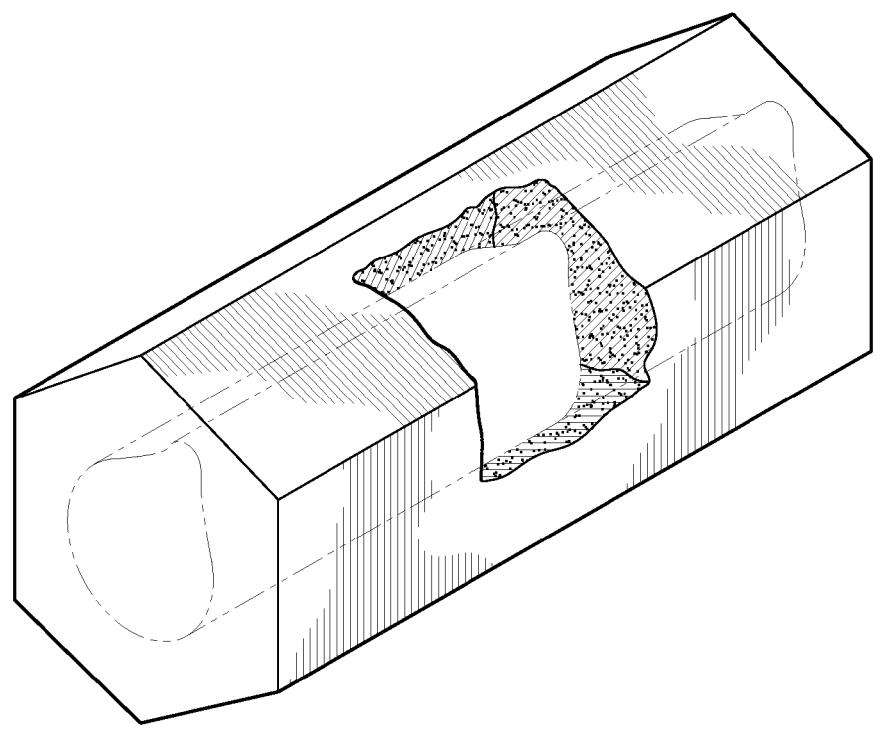
FIGS. 1C-E are variations of FIG. 1A or 1B showing different possible geometries of the outer sheath in combination with an inner core, shown in phantom line, which can have any core-lobe geometry.
Figure 1D:
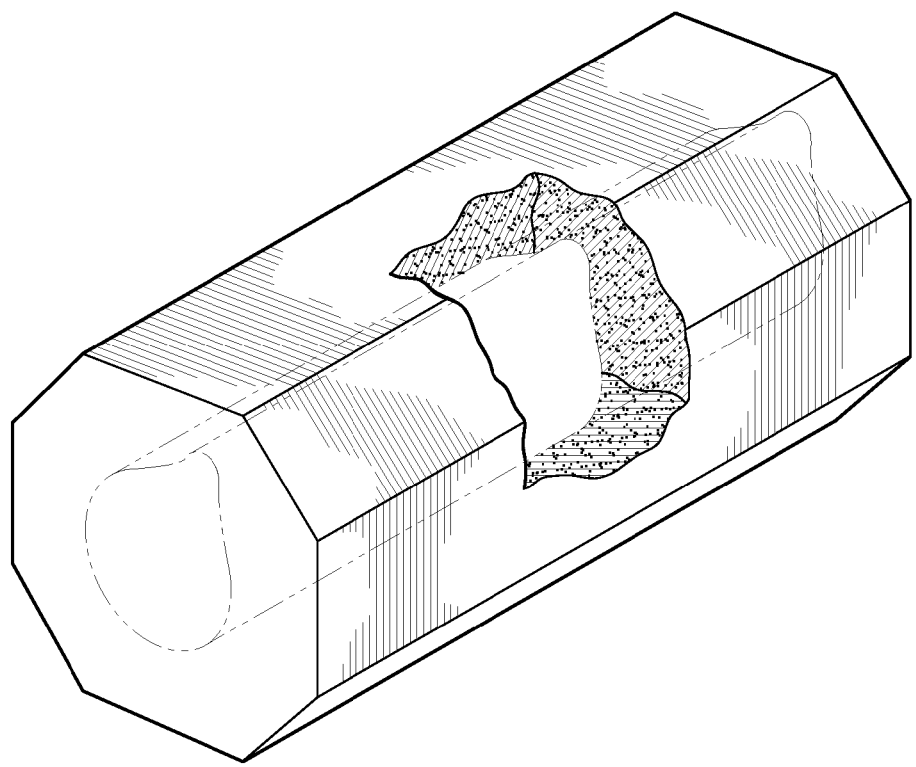
Figure 1E:
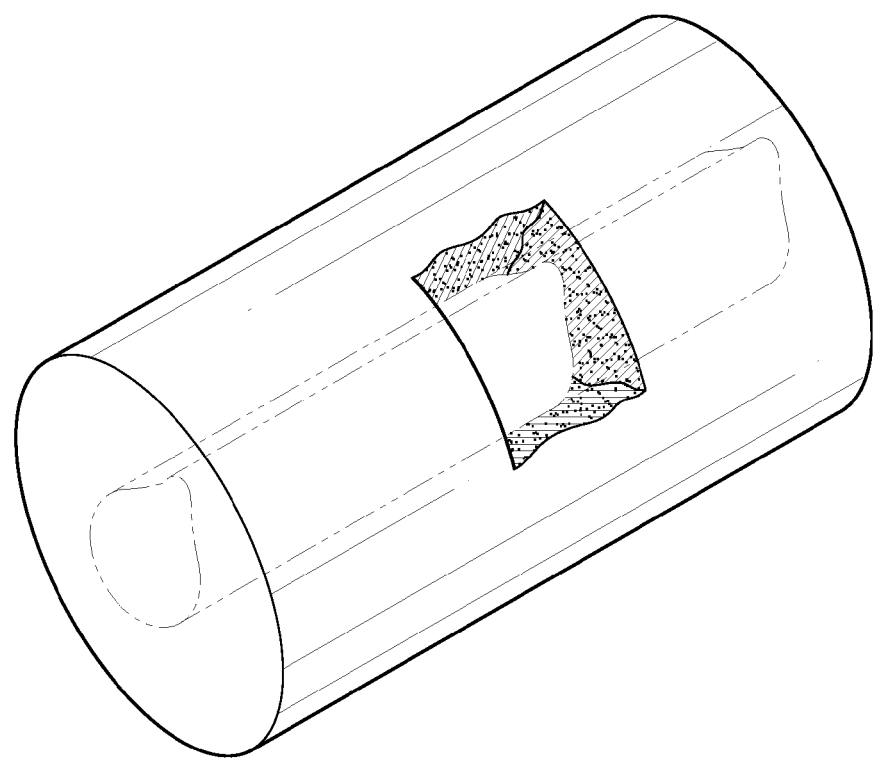

Outer sheath 12A (and 12B) is represented with a phantom line to indicate that the geometry of outer sheath 12A is not restrictive. Outer sheath 12A can have any geometry. Variations in FIGS. 1A and 1B can include a hexagonal outer sheath (FIG. 1C), octagonal outer sheath (FIG. 1D), or cylindrical (or ovoid) outer sheath (FIG. 1E), for example, with all other elements being the same as in FIGS. 1A and 1B (outer sheath 12, sheath surface 14, end surface 16, inner core 18, core surface 20, lobe surface 24, and end surface 26).

Figure 2A:
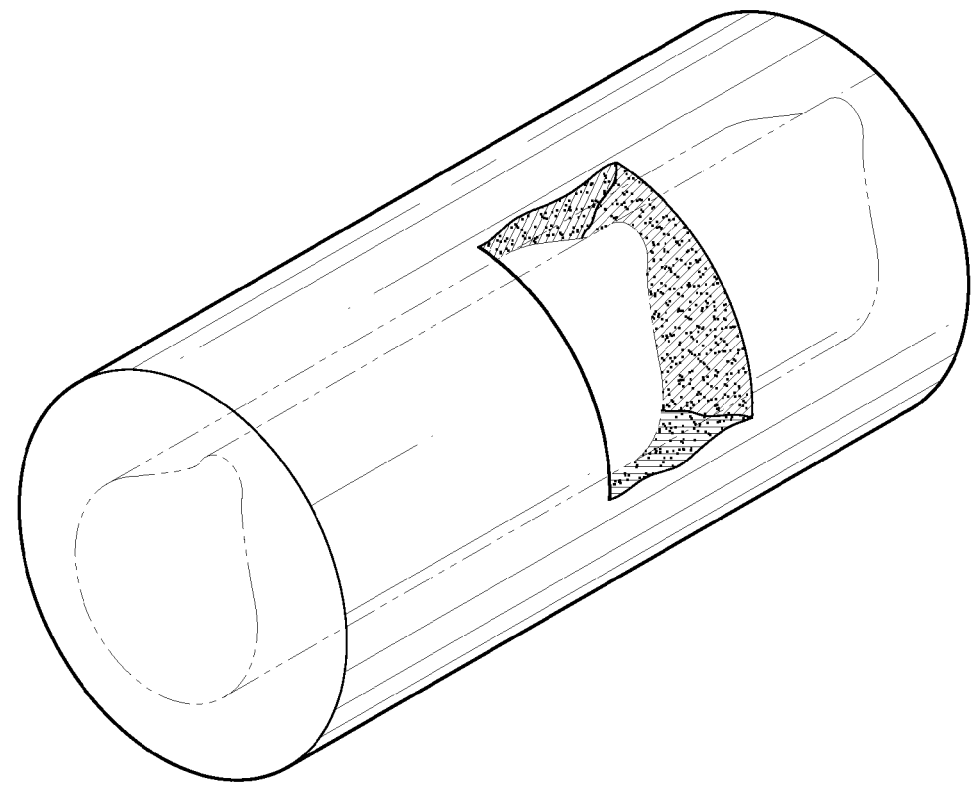
FIG. 2A is a variation of FIG. 1A or 1B showing the inner core in phantom line. Various inner core geometries are shown in FIGS. 2B-2E.
Figure 2B:
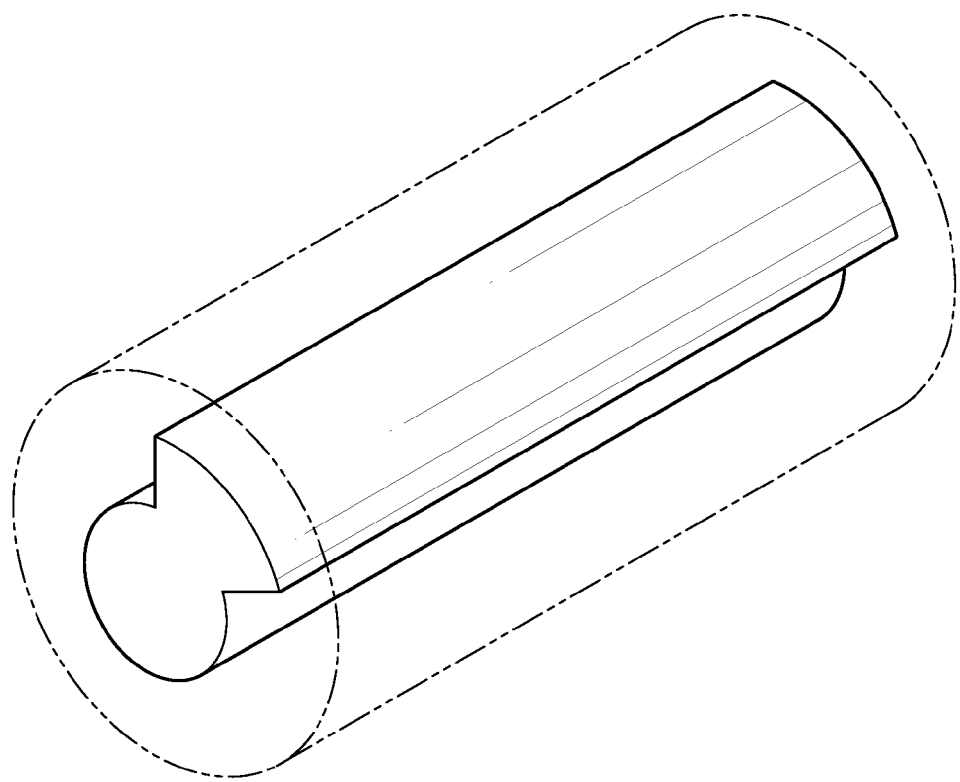
Figure 2C:
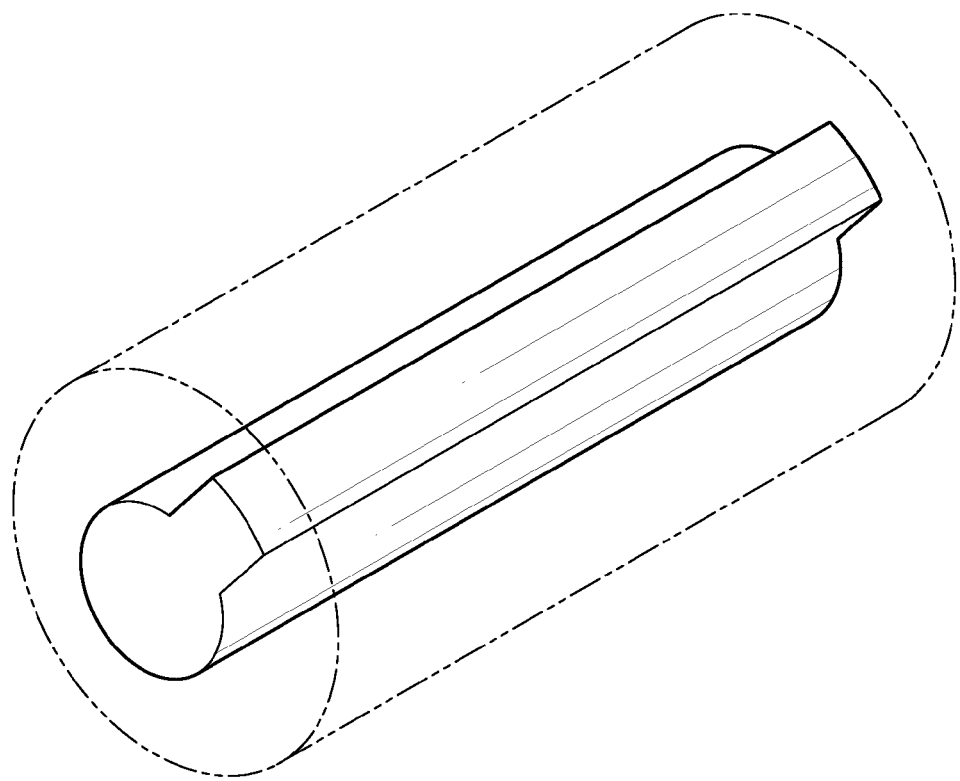
Figure 2D:
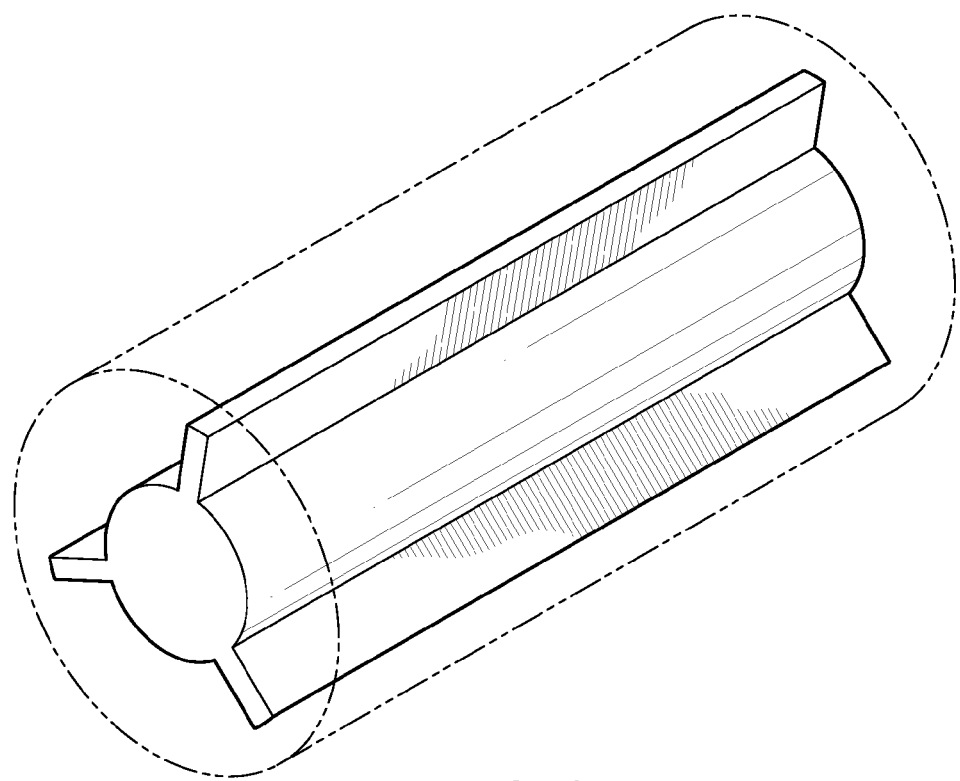
Figure 2E:
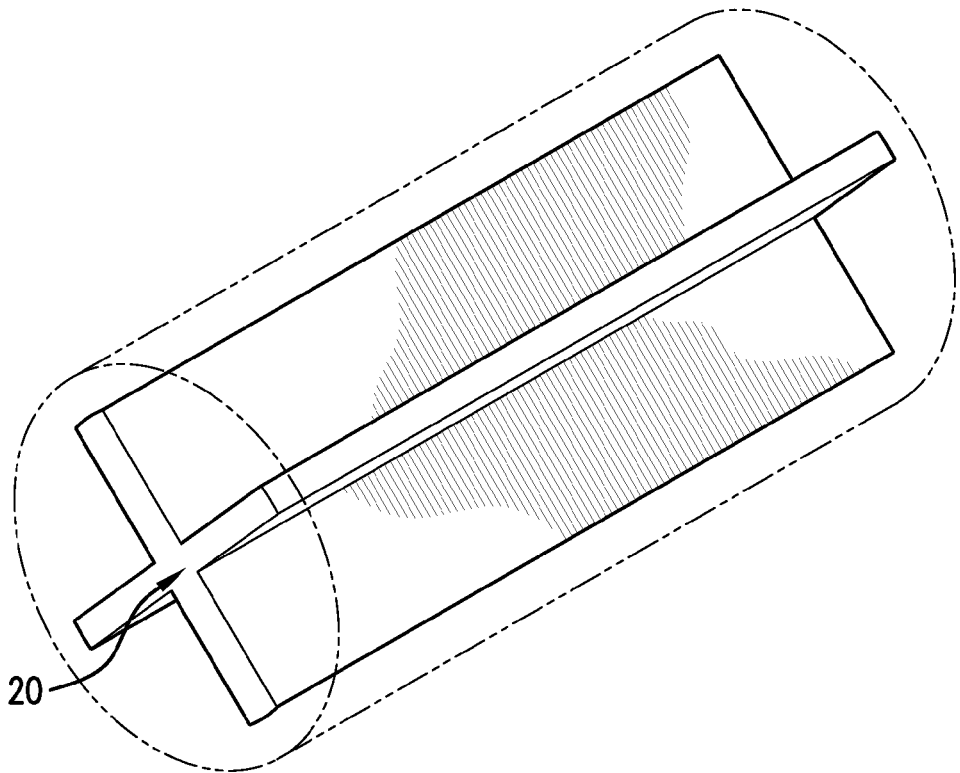

Similarly, with reference to FIG. 2A, the inner core is represented with a phantom line to indicate that the inner core can have any core-lobe geometry. The inner core is also represented by phantom lines in FIGS. 1C-E to indicate that any inner core-lobe geometry can be used with any outer sheath geometry. A few non-limiting examples of inner core geometries are shown in FIGS. 2B-E, which again show the outer core in phantom line, with all other elements being the same as in FIGS. 1A and 1B (outer sheath 12, sheath surface 14, end surface 16, inner core 18, core surface 20, lobe surface 24, and end surface 26). With reference to FIGS. 2D and 2E, more than one longitudinal lobe can extend outwardly at least partially through the outer sheath. The inner core longitudinal surface in FIG. 2E is the inner core surface where the lobes meet (20).

The outer sheath and in some instances the inner core comprises a biocompatible polymer that can also be biodegradable. The molecular weight of a polymer can be important given that molecular weight influences the biodegradation rate of a biodegradable polymer. For a diffusion mechanism of bioactive agent release, the polymer can remain intact until all of the drug is released from the polymer and then degrade. The drug can also be released from the polymer as the polymer erodes. By an appropriate selection of polymer, a formulation can be made such that the resulting polymer exhibits both diffusion release and biodegradation release. Molecular weights can be measured by methods known in the art, including gel permeation chromatography, viscosity, light-scattering, and other methods.

The polymer can be formulated so as to degrade within a desired time interval, once present in a subject, or a biological medium. For example, the time interval can be from about less than one day to about 1 month. Longer time intervals can extend to 6 months, including for example, polymers that degrade from about $\geqq 0$ to about 6 months, or from about 1 to about 6 months. The polymer can also degrade in longer time intervals, up to 2 years or longer, including, for example, from about $\geqq 0$ to about 2 years, or from about 1 month to about 2 years.

The desired bioactive agent release mechanism can influence the selection of the polymer or the design of the implant device. A biocompatible polymer, for example, can be selected so as to release or allow the release of a bioactive agent at a desired lapsed time after the implant device has been implanted in a subject. For example, the polymer can be selected to release or allow the release of the bioactive agent prior to the bioactive agent beginning to diminish its activity, as the bioactive agent begins to diminish in activity, when the bioactive agent is partially diminished in activity, for example at least 25%, at least 50% or at least 75% diminished, when the bioactive agent is substantially diminished in activity, or when the bioactive agent is completely gone or no longer has activity.

Examples of suitable polymers to be included in the sheath or core include without limitation polyesters, polyhydroxyalkanoates, polyhydroxybutyrates, polydioxanones, polyhydroxyvalerates, polyanhydrides, polyorthoesters, polyphosphazenes, polyphosphates, polyphosphoesters, polydioxanones, polyphosphoesters, polyphosphates, polyphosphonates, polyphosphates, polyhydroxyalkanoates, polycarbonates, polyalkylcarbonates, polyorthocarbonates, polyesteramides, polyamides, polyamines, polypeptides, polyurethanes, polyalkylene alkylates, polyalkylene oxalates, polyalkylene succinates, polyhydroxy fatty acids, polyacetals, polycyanoacrylates, polyketals, polyetheresters, polyethers, polyalkylene glycols, polyalkylene oxides, polyethylene glycols, polyethylene oxides, polypeptides, polysaccharides, or polyvinyl pyrrolidones. Other non-biodegradable but durable polymers include without limitation ethylene-vinyl acetate co-polymer, polytetrafluoroethylene, polypropylene, polyethylene, and the like. Likewise, other suitable non-biodegradable polymers include without limitation silicones and polyurethanes.

The implant device can comprise a variety of polysaccharides such as cellulose, modified cellulose including ethyl cellulose, hydroxyethyl cellulose, hydroxypropyl cellulose, methylcellulose, or hydroxypropylmethyl cellulose. The implant device can also comprise amylase, starch, maltodextrin, glycogen, chitin, or modified polysaccharides such as hydrophobically-modified polysaccharides. Examples of hydrophobically-modified polysaccharides include maltodextrins that have been hydrophobically-modified with $C_1$-$C_{10}$ alkyl sidechains, saturated sidechains, unsaturated sidechains, fatty acid side chains, or the like.

Other specific examples of suitable polymers include CAMEO polymers (ester-amide polymers), POLYACTIVE polymers, and SYNBIOSYS polymers (ester-urethane polymers. Further examples include polyesters with or without side-chains including poly(glycolide), poly(lactide), which has a pendent methyl group, and glycolides having $C_2$-$C_{12}$ side chains, such as hexyl-modified glycolide.

Further specific examples of suitable polymers include one or more of a poly(lactide), a poly(glycolide), a poly(lactide-co-glycolide), a poly(caprolactone), a poly(orthoester), a poly(phosphazene), a poly(hydroxybutyrate) or a copolymer containing a poly(hydroxybutarate), a poly(lactide-co-caprolactone), a polycarbonate, a polyesteramide, a polyanhydride, a poly(dioxanone), a poly(alkylene alkylate), a copolymer of polyethylene glycol and a polyorthoester, a biodegradable polyurethane, a poly(amino acid), a polyamide, a polyesteramide, a polyetherester, a polyacetal, a polycyanoacrylate, a poly(oxyethylene)/poly(oxypropylene) copolymer, polyacetals, polyketals, polyphosphoesters, polyhydroxyvalerates or a copolymer containing a polyhydroxyvalerate, polyalkylene oxalates, polyalkylene succinates, poly(maleic acid), and copolymers, terpolymers, combinations, or blends thereof.

Copolymers can also be used, examples of which are those that comprise one or more blocks of hydrophilic or water soluble polymers, including, but not limited to, polyethylene glycol, (PEG), or polyvinyl pyrrolidone (PVP), in combination with one or more blocks another biocompatible or biodegradable polymer that comprises lactide, glycolide, caprolactone, or a combination thereof.

The polymer can comprise one or more residues of lactic acid, glycolic acid, lactide, glycolide, caprolactone, hydroxybutyrate, hydroxyvalerates, dioxanones, polyethylene glycol (PEG), polyethylene oxide, or a combination of these. Lactide-based polymers can comprise any lactide residue, including all racemic and stereospecific forms of lactide, including L-lactide, D-lactide, and D,L-lactide, or a mixture thereof. Useful polymers comprising lactide include, but are not limited to poly(L-lactide), poly(D-lactide), and poly(DL-lactide); and poly(lactide-co-glycolide), including poly(L-lactide-co-glycolide), poly(D-lactide-co-glycolide), and poly(DL-lactide-co-glycolide); or copolymers, terpolymers, combinations, or blends of these polymers. Lactide/glycolide polymers can be conveniently made by melt polymerization through ring opening of lactide and glycolide monomers. Additionally, racemic DL-lactide, L-lactide, and D-lactide polymers are commercially available. The L-polymers are more crystalline and resorb slower than DL-polymers. In addition to copolymers comprising glycolide and DL-lactide or L-lactide, copolymers of L-lactide and DL-lactide are commercially available. Homopolymers of lactide or glycolide are also commercially available.

When the biodegradable polymer is poly(lactide-co-glycolide), or a mixture of poly(lactide) and poly(glycolide), the amount of lactide and glycolide in the polymer can vary. For example, the biodegradable polymer can contain 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. For example, the biodegradable polymer can be poly(lactide), 95:5 poly(lactide-co-glycolide) 85:15 poly(lactide-co-glycolide), 75:25 poly(lactide-co-glycolide), 65:35 poly(lactide-co-glycolide), or 50:50 poly(lactide-co-glycolide), where the ratios are mole ratios.

The polymer can also be a poly(caprolactone) or a poly(lactide-co-caprolactone). For example, the polymer can be a poly(lactide-caprolactone) such as 95:5 poly(lactide-co-caprolactone), 85:15 poly(lactide-co-caprolactone), 75:25 poly(lactide-co-caprolactone), 65:35 poly(lactide-co-caprolactone), or 50:50 poly(lactide-co-caprolactone), where the ratios are mole ratios.

The inner core or the outer sheath can comprise a bioactive agent. When both the inner core and outer sheath comprise a bioactive agent, the bioactive agent can be the same or different and can be present in the same or different amounts. For some therapies it can be desirable to have a bioactive agent only in the inner core. A large variety of bioactive agents can be used. Typically, the bioactive agent is one that can be released from the implant device, usually as the device degrades or bioerodes, but can also release through a simple diffusion mechanism, as discussed above. The processing of a polymer and bioactive agent can be performed under conditions such that the agent is intimately mixed or dispersed throughout the polymer, e.g., homogenously or substantially homogenously. Alternatively, the processing of a polymer and bioactive agent can be performed under conditions such that the agent is localized on or in only a portion of device. Thus, the polymer can include areas that are rich in bioactive agent and areas that are not as rich. The device can comprise a large number of bioactive agents either singly or in combination.

Various forms of the bioactive agent can be used, which are capable of being released into adjacent tissues or fluids. A liquid or solid bioactive agent can be used. The bioactive agents can include salts of the active ingredient. As such, the bioactive agents can be acidic, basic, or amphoteric salts. They can be nonionic molecules, polar molecules, or molecular complexes capable of hydrogen bonding. The bioactive agent can be included in the compositions in the form of, for example, an uncharged molecule, a molecular complex, a salt, an ether, an ester, an amide, polymer drug conjugate, or other form to provide the effective biological or physiological activity.

Examples of bioactive agents include without limitation small molecules, peptides, proteins such as hormones, enzymes, antibodies, receptor binding proteins, antibody fragments, antibody conjugates, nucleic acids such as aptamers, iRNA, siRNA, microRNA, DNA, RNA, antisense nucleic acid or the like, antisense nucleic acid analogs or the like, VEGF inhibitors, macrocyclic lactones, dopamine agonists, dopamine antagonists, low-molecular weight compounds, high-molecular-weight compounds, or conjugated bioactive agents.

Other bioactive agents can include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, antipsychotics, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Still other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Representative drugs that can be used as bioactive agents include, but are not limited to, peptide drugs, protein drugs, therapeutic antibodies, anticalins, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, anti-inflammatory agents, nonsteroidal anti-inflammatory agents, antiparkinsonian agents, antihypertensive agents, -adrenergic blocking agents, nutritional agents, anti-TNF agents and the benzophenanthridine alkaloids. The agent can further be a substance capable of acting as a stimulant, sedative, hypnotic, analgesic, anticonvulsant, and the like.

Other bioactive agents include but are not limited to analgesics such as acetaminophen, acetylsalicylic acid, and the like; anesthetics such as lidocaine, xylocalne, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenyloin sodium, diazepam, and the like; antidepressants such as isocarboxazid, amoxapine, and the like; antihistamines such as diphenhydramine HCl, chlorpheniramine maleate, and the like; antipsychotics such as clozapine, haloperidol, carbamazepine, gabapentin, topimarate, bupropion, sertraline, alprazolam, buspirone, risperidone, aripiprazole, olanzapine, quetiapine, ziprasidone, iloperidone, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin B12, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, Enbrel®, Rituxan®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; anti-malarials, L-dopa, diuretics such as furosemide, spironolactone, and the like; antiulcer drugs such as rantidine HCl, cimetidine HCl, and the like.

The bioactive agent can also be an immunomodulator, including, for example, cytokines, interleukins, interferon, colony stimulating factor, tumor necrosis factor, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans. Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In some examples, the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin, Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Cotrimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Timidazole, Ropinerole, Ivermectin, Moxidectin, Afamelanotide, Cilengitide, or a combination thereof. In one aspect, the bioactive agent can be a combination of Rifampicin (Rifampin in U.S.) and Minocycline.

The amount of bioactive agent incorporated into the implant device varies depending upon the particularly agent, the desired therapeutic affect, and the desired time span. Since a variety of devices in a variety of sizes and shapes are intended to provide dosage regimens for a variety purposes, there is no critical upper limit in the amount of drug incorporated into the device. The lower limit too will depend upon the activity of the drug and the time span of its release from the device. Those skilled in the pharmaceutical arts will know how to determine toxic levels of a given drug as well as the minimum effective dose.

It is contemplated that other components such as excipients, pharmaceutically carriers or adjuvants, microparticles, and so forth, can be combined with the polymer or polymers of the implant device. Thus, the bioactive agent can be present as a component in a pharmaceutical composition. Pharmaceutical compositions can be conveniently prepared in a desired dosage form, including, for example, a unit dosage form or controlled release dosage form, and prepared by any of the methods well known in the art of pharmacy. In general, pharmaceutical compositions are prepared by uniformly and intimately bringing the bioactive agent into association with a liquid carrier or a finely divided solid carrier, or both. The pharmaceutical carrier employed can be a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. Other pharmaceutically acceptable carriers or components that can be mixed with the bioactive agent can include, for example, a fatty acid, a sugar, a salt, a water-soluble polymer such as polyethylene glycol, a protein, polysachamide, or carboxmethyl cellulose, a surfactant, a plasticizer, a high- or low-molecular-weight porosigen such as polymer or a salt or sugar, or a hydrophobic low-molecular-weight compound such as cholesterol or a wax.

The polymer of the core or sheath and bioactive agent, or just the bioactive agent alone (optionally present with other adjuvents), can be combined to form a blend or admixture. Admixing methods can be performed using techniques known in the art. For example, the polymer and bioactive agent can be dry blended (i.e., mixing of particulates of the polymer and the agent) using, for example, a Patterson-Kelley V-blender, or granulated prior to being incorporated into the device. Solution processing can also be used.

To form the implant device, a variety of methods can be used. The implants can be prepared by co-extrusion methods, for example through heat extrusion or melt extrusion using appropriately shaped dyes for the inner core and outer sheath. The bioactive agent and any polymer or other adjuvent of the inner core can be blended, for example using a Turbula Shaker Mixer Type T2 F (available from a number of commercial sources, including Artisan Scientific Corporation 301 E. Mercury Drive Champaign, Ill. 61822). The blend can be dried, formed into a film, or formed into another appropriate solid and subsequently co-extruded along with the outer sheath, which can be similarly processed. In other examples, the drug and polymer can be dissolved to form a dispersion. The solvent can then be evaporated, and then the remaining solid can be fed into the extruder. The bioactive agent and any polymer of the inner core can also be added separately to the extruder and subsequently combined and blended during the extrusion process.

The blend can be extruded using a suitable extrusion device. Examples include single-screw extruders, such as a RANDCASTLE extruder (Cedar Grove, N.J., U.S.A.), twin-screw extruders, or combinations of extruders. The implant device can be prepared using a single pass through an extruder, or extrusion can be performed multiple times to further blend or process the bioactive agent and any polymer or other adjuvant present.

Once a particular design of implant device is selected for a targeted application, the appropriate dyes for the inner and outer core of the implant device can be milled using methods known in the art and subsequently installed in the extruder. The extruded formulation can also be prepared by the "drawing" technique, wherein the extruded article is pulled or "drawn" out at a rate that is slightly faster than the actual rate of extrusion.

After extrusion, the implant device can be further processed. Multiple implant devices can be prepared from a single extruded article by cutting the extruded article into more than one segment. When the bioactive agent is homogenously distributed in the inner core (or outer sheath) of the extruded article, the size of the segment of the extruded article will determine the amount of bioactive agent in that segment and will therefore affect the release profile of the segment. The surface area of the segment will also likewise affect the release profile of the bioactive agent. Surface treatment methods, such as those described in US 2006/0029637 (application Ser. No. 11/196,591) to Tice et al., can be used to achieve further alterations in the bioactive agent release mechanism.

Multiple implant devices can be prepared from a single extruded article by cutting the extruded article into a plurality of disconnected segments and the plurality of segments can then be administered to a subject. The release profile of the plurality of segments, in this aspect, can be affected by size, surface area, and surface treatment (if any), among other variables. For example, if a single extruded article is cut into a 1 cm, 2 cm, and 3 cm segments, the release profile exhibited by the cut segments will be different than a release profile exhibited by the single extruded article (6 cm) and will also likely be different than three 3 cm segments prepared from the same 6 cm extruded article. It will be apparent however, in other aspects, that the plurality of implant devices can comprise individual implant devices prepared from more than one extruded article and can have release profiles that are the same or different than each other.

The implant devices or compositions comprising the implant devices of the invention can be used as delivery vehicles to deliver the bioactive agent to any subject, such as a human. Dosages and particular formulations can be determined by one of skill in the pharmaceutical arts and will vary widely depending on the indication being treated.

Various modifications and variations can be made to the devices and methods described. Other aspects of the devices and methods will be apparent from consideration of the specification and use or practice of the devices and methods. It is intended that the specification and examples be considered as exemplary.

What is claimed is:

1. An implant device, comprising:
   a. an outer sheath comprising a biocompatible polymer and having an exposed longitudinal sheath surface and exposed proximal and distal end surfaces; and
   b. an inner core comprising a bioactive agent and having:
      i. a longitudinal core surface that is completely surrounded by the sheath; and
      ii. a longitudinal lobe extending outwardly from the longitudinal core surface at least partially through the outer sheath and having a longitudinal lobe surface; wherein at least a portion of the longitudinal lobe surface is closer to the exposed longitudinal sheath surface than any portion of the longitudinal core surface.

2. The implant device of claim 1, wherein the inner core has an exposed proximal core end surface or an exposed distal core end surface.

3. The implant device of claim 1, wherein the implant device is cylindrical.

4. The implant device of claim 1, wherein the inner core is substantially coextensive with the outer sheath.

5. The implant device of claim 1, wherein the longitudinal lobe extends only partially through the outer sheath.

6. The implant device of claim 1, wherein a portion of the longitudinal lobe surface is surrounded by the outer sheath, and a portion of the longitudinal lobe surface is exposed.

7. The implant device of claim 1, wherein the biocompatible polymer of the outer sheath comprises poly(lactide), poly(glycolide), poly(caprolactone), poly(lactide-co-glycolide), or a copolymer, mixture, or blend thereof.

8. The implant device of claim 1, wherein the inner core comprises a biocompatible polymer that is the same as or different from the biocompatible polymer of the outer sheath.

9. The implant device of claim 8, wherein the biocompatible polymer of the inner core comprises poly(lactide), poly(glycolide), poly(caprolactone), poly(lactide-co-glycolide), or a copolymer, mixture, or blend thereof.

10. The implant device of claim 1, wherein the outer sheath comprises a bioactive agent that is the same as or different from the bioactive agent of the inner core.

* * * * *